(12) United States Patent
Wu et al.

(10) Patent No.: US 12,417,609 B2
(45) Date of Patent: Sep. 16, 2025

(54) METHOD, SYSTEM AND COMPUTER-READABLE STORAGE MEDIUM FOR CATEGORIZING AND ADJUSTING ORIENTATION OF CLINICAL IMAGE

(71) Applicant: KAOHSIUNG CHANG GUNG MEMORIAL HOSPITAL, Kaohsiung (TW)

(72) Inventors: Te-Ju Wu, Kaohsiung (TW); Tzuo-Yau Fan, Taoyuan (TW); Yueh-Peng Chen, Taoyuan (TW); Chin-Yi Ji, Kaohsiung (TW); Chang-Fu Kuo, Taoyuan (TW)

(73) Assignee: KAOHSIUNG CHANG GUNG MEMORIAL HOSPITAL, Kaohsiung (TW)

( * ) Notice: Subject to any disclaimer, the term of this patent is extended or adjusted under 35 U.S.C. 154(b) by 338 days.

(21) Appl. No.: 18/158,541

(22) Filed: Jan. 24, 2023

(65) Prior Publication Data
US 2023/0281944 A1    Sep. 7, 2023

(30) Foreign Application Priority Data
Mar. 4, 2022    (TW) .................................. 111107894

(51) Int. Cl.
*G06V 10/24* (2022.01)
*G06T 5/50* (2006.01)
(Continued)

(52) U.S. Cl.
CPC .............. *G06V 10/242* (2022.01); *G06T 5/50* (2013.01); *G06V 10/44* (2022.01); *G06V 10/82* (2022.01);
(Continued)

(58) Field of Classification Search
CPC ...... G06V 10/242; G06V 10/44; G06V 10/82; G06V 10/43; G06V 2201/03;
(Continued)

(56) References Cited

U.S. PATENT DOCUMENTS

2019/0251336 A1*  8/2019  Wu .......................... G06F 18/22
2023/0326016 A1*  10/2023  Zhang .................. G06V 10/764
                                                         382/128

\* cited by examiner

*Primary Examiner* — Stephen R Koziol
*Assistant Examiner* — Michael Kim Maiden
(74) *Attorney, Agent, or Firm* — Osha Bergman Watanabe & Burton LLP

(57) ABSTRACT

A method for categorizing and adjusting an orientation of a clinical image is implemented using a system that includes a categorization module and a plurality of orientation modules. The method includes: in response to receipt of the clinical image, performing, by the categorization module, a categorization operation so as to categorize the clinical image into one of a plurality of predetermined categories; transmitting the clinical image to a corresponding one of the plurality of orientation modules based on a result of the categorization operation; and performing, by the corresponding one of the plurality of orientation modules, an orientation adjusting operation for adjusting the orientation of the clinical image. For a clinical image that is a facial image and for a clinical image that is an intra-oral image, different orientation adjusting operations may be performed, so as to generate an adjusted image that is properly oriented.

9 Claims, 9 Drawing Sheets

(51) Int. Cl.
  *G06V 10/44* (2022.01)
  *G06V 10/82* (2022.01)
  *G16H 30/40* (2018.01)
(52) U.S. Cl.
  CPC ... *G16H 30/40* (2018.01); *G06T 2207/20132* (2013.01); *G06T 2207/20221* (2013.01); *G06T 2207/30036* (2013.01); *G06T 2207/30168* (2013.01); *G06V 2201/07* (2022.01)
(58) Field of Classification Search
  CPC ...... G06V 10/764; G06V 40/171; G06T 5/50; G06T 2207/20221; G06T 2207/30036; G06T 2207/30168; G16H 30/40
  See application file for complete search history.

METHOD, SYSTEM AND COMPUTER-READABLE STORAGE MEDIUM FOR CATEGORIZING AND ADJUSTING ORIENTATION OF CLINICAL IMAGE

CROSS-REFERENCE TO RELATED APPLICATION

This application claims priority to Taiwanese Patent Application No. 111107894, filed on Mar. 4, 2022.

FIELD

The disclosure relates to a method, a system and computer-readable storage medium for categorizing, adjusting an orientation of, and ranking a clinical image.

BACKGROUND

In the field of dentistry, including the works of orthodontics, multiple clinical images of a patient are typically employed for various use such as to assist diagnosis, to record a condition and/or a progress of the patient, to facilitate communication between dentists/orthodontists and the patient, to submit a claim for insurance payment, for clinical education purposes, or to make a presentation, etc.

In general, in order to obtain all information for performing a diagnosis, as many as about twenty clinical images of the patient may be taken, from different directions and focusing on different parts of the patient. Afterward, in order to manage the clinical images relating to a large number of patients, and for the sake of subsequent processing, a number of pre-processing operations may be manually performed on the clinical images, including categorizing the clinical images, adjusting each of the clinical images to a specific orientation, cropping the clinical images to a predetermined size, etc.

SUMMARY

Therefore, an object of the disclosure is to provide a method for automatically categorizing a number of clinical images, and for adjusting orientations of the clinical images that have been categorized.

According to one embodiment of the disclosure, the method is implemented using a system that includes a categorization module and a plurality of orientation modules, the method includes:

a) in response to receipt of the clinical image, performing, by the categorization module, a categorization operation so as to categorize the clinical image into one of a plurality of predetermined categories;

b) transmitting the clinical image to a corresponding one of the plurality of orientation modules based on a result of the categorization operation; and c) performing, by the corresponding one of the plurality of orientation modules, an orientation adjusting operation for adjusting the orientation of the clinical image.

In the embodiment, the orientation adjusting operation includes different operations in the case where it is determined, based on the categorization operation, that the clinical image is a facial image and in the case where that the clinical image is an intra-oral image.

in the case where it is determined that the clinical image is a facial image, the orientation adjusting operation includes identifying an object in the clinical image,
identifying two feature points on the object,
generating a feature line that connects the two feature points, and a reference line that passes through one of the two feature points, that extends in parallel with an axis associated with a reference coordinate system of the clinical image,
determining whether the feature line and the reference line overlap each other, and
in the case where the feature line and the reference line are determined as not overlapping each other, rotating the clinical image, using the one of the two feature points through which the reference line passes as a pivot, to the point where the feature line overlaps the reference line, so as to generate an adjusted image, in the case where it is determined that the clinical image is an intra-oral image, the orientation adjusting operation includes identifying an object in the clinical image,
identifying a feature area of the clinical image that encloses the object, based on a contour of the object,
generating a feature line that divides the object into an upper part and a lower part, and generating a reference line that extends in parallel with one of an X axis and a Y axis associated with the reference coordinate system of the clinical image,
determining whether the feature line and the reference line overlap each other,
in the case where it is determined that the feature line and the reference line do not overlap each other, rotating the clinical image using an intersection point of the feature line and the reference line as a pivot, to the point where the feature line and the reference line overlap each other, so as to generate an adjusted image.

In some aspects, the system further includes a ranking module connected to each of the plurality of orientation modules. After an adjusted image is generated by one of the orientation modules, the ranking module is configured to determine a rotation angle of the adjusted image relative to the original clinical image, and assign an associated rank to the original clinical image. In some embodiments, the ranking module is configured to determine whether an image has a low quality, and in such a case, proceed to assign a lower rank to the image, indicating that the image has a low quality.

Another object of the disclosure is to provide a system that is configured to perform the above-mentioned method.

According to the disclosure, the system includes a categorization module, a plurality of orientation modules connected to the categorization module, and a data storage module that stores the clinical therein.

In response to receipt of the clinical image, the categorization module is configured to perform a categorization operation so as to categorize the clinical image into one of a plurality of predetermined categories, and to transmit the clinical image to a corresponding one of the plurality of orientation modules based on a result of the categorization operation.

The corresponding one of the plurality of orientation modules is configured to perform an orientation adjusting operation for adjusting the orientation of the clinical image.

In the embodiment, the orientation adjusting operation includes different operations in the case where it is determined, based on the categorization operation, that the clinical image is a facial image and in the case where that the clinical image is an intra-oral image.

In the case that it is determined that the clinical image is a facial image, the orientation adjusting operation includes
   identifying an object in the clinical image,
   identifying two feature points on the object,
   generating a feature line that connects the two feature points and a reference line that passes through one of the two feature points, that extends in parallel with an axis associated with a reference coordinate system of the clinical image,
   determining whether the feature line and the reference line overlap each other, and
   in the case that the feature line and the reference line are determined as not overlapping each other, rotating the clinical image, using the one of the two feature points through which the reference line passes as a central point of rotation, to the point that the feature line overlaps the reference line, so as to generate an adjusted image.

In the case that it is determined that the clinical image is an intra-oral image, the orientation adjusting operation includes
   identifying an object in the clinical image,
   identifying a feature area of the clinical image that encloses the object, based on a contour of the object,
   generating a feature line that divides the object into an upper part and a lower part, and generating a reference line that extends in parallel with one of an X axis and a Y axis associated with the reference coordinate system of the clinical image,
   determining whether the feature line and the reference line overlap each other, and
   in the case that it is determined that the feature line and the reference line do not overlap each other, rotating the clinical image using an intersection point of the feature line and the reference line as a central point of rotation, to the point that the feature line and the reference line overlap each other, so as to generate an adjusted image.

In some aspects, the system further includes a ranking module connected to each of the plurality of orientation modules. The method may further include, after an adjusted image is generated by one of the orientation modules, determining, by the ranking module, a rotation angle of the adjusted image relative to the original clinical image, and assigning an associated rank to the original clinical image. In some embodiments, the method further includes to determine whether an image has a low quality, and proceeds to assign a lower rank to the image, indicating that the image has a low quality.

Another object of the disclosure is to provide a non-transitory machine readable storage medium storing instructions that, when executed by a processor of a computer device, cause the processor to perform steps of the above-mentioned method.

BRIEF DESCRIPTION OF THE DRAWINGS

Other features and advantages of the disclosure will become apparent in the following detailed description of the embodiments with reference to the accompanying drawings. It is noted that various features may not be drawn to scale.

DETAILED DESCRIPTION

Figure 1:
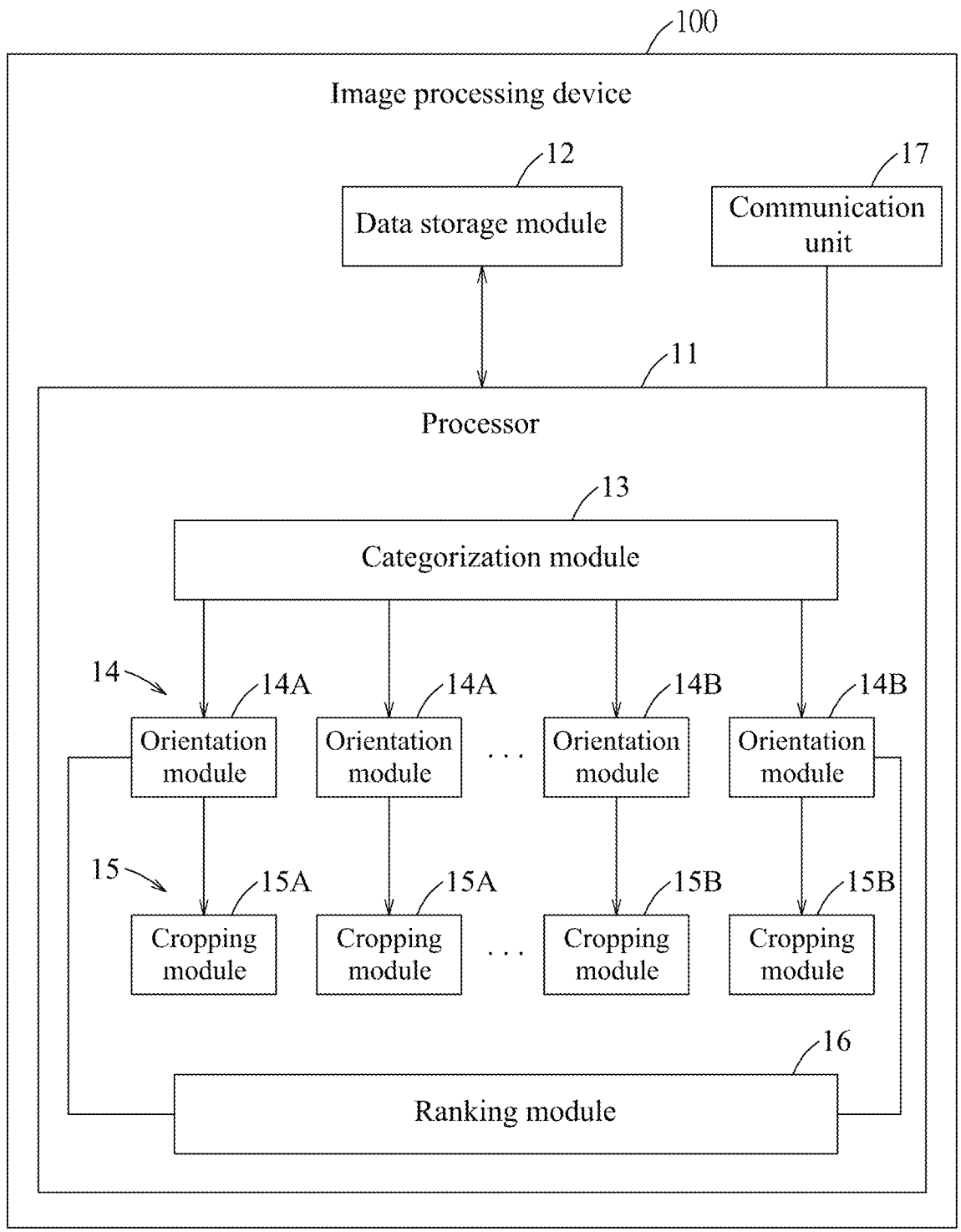
FIG. 1 is a block diagram illustrating components of a system for image processing according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Throughout the disclosure, the term "coupled to" or "connected to" may refer to a direct connection among a plurality of electrical apparatus/devices/equipment via an electrically conductive material (e.g., an electrical wire), or an indirect connection between two electrical apparatus/devices/equipment via another one or more apparatus/devices/equipment, or wireless communication.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

FIG. 1 is a block diagram illustrating components of a system for image processing according to one embodiment of the disclosure. In this embodiment, the system includes an image processing device 100. The image processing device 100 may be embodied using a computer device such as a personal computer, a server, a cloud server that can be accessed online, etc. The image processing device 100 includes a processor 11, a data storage module 12 electrically connected to the processor 11, a categorization module 13, a plurality of orientation modules 14, a plurality of cropping modules 15, and a communication unit 17 electrically connected to the processor 11.

The processor 11 may include, but not limited to, a single core processor, a multi-core processor, a dual-core mobile processor, a microprocessor, a microcontroller, a digital signal processor (DSP), a field-programmable gate array (FPGA), an application specific integrated circuit (ASIC), and/or a radio-frequency integrated circuit (RFIC), etc.

The data storage module 12 may be embodied using, for example, random access memory (RAM), read only memory (ROM), programmable ROM (PROM), firmware, and/or flash memory, etc.

In this embodiment, each of the categorization module 13, the plurality of orientation modules 14, and the plurality of cropping modules 15 may be embodied using firmware instructions stored in the data storage module 12 or in the processor 11, as shown in FIG. 1.

In some embodiments, each of the categorization module 13, the plurality of orientation modules 14, and the plurality of cropping modules 15 may be embodied using software instructions that can be integrated into a software application stored in the data storage module 12. When executed by the processor 11, the software application causes the processor 11 to perform operations as described in the following paragraphs.

In use, the categorization module 13 is connected to each of the plurality of orientation modules 14, and each of the plurality of orientation modules 14 is connected to a respective one of the cropping modules 15.

The communication unit 17 may include one or more of a radio-frequency integrated circuit (RFIC), a short-range wireless communication module supporting a short-range wireless communication network using a wireless technology of Bluetooth® and/or Wi-Fi, etc., and a mobile communication module supporting telecommunication using Long-Term Evolution (LTE), the third generation (3G), the fourth generation (4G) or fifth generation (5G) of wireless mobile telecommunications technology, or the like.

In some embodiments, each of the categorization module 13, the plurality of orientation modules 14, and the plurality of cropping modules 15 may be embodied using circuitry components that can be integrated into an application-specific integrated circuit (ASIC), a programmable logic device (PLD) or other hardware components that may be connected to or included in the processor 11 for performing the corresponding operations.

It is noted that in some embodiments, each of the categorization module 13, the plurality of orientation modules 14, and the plurality of cropping modules 15 may be embodied using components that are separated from one another. For example, the system may include multiple computing devices, and the categorization module 13, the plurality of orientation modules 14, and the plurality of cropping modules 15 may be implemented in three different computing devices. As such, data transmission among the categorization module 13, the plurality of orientation modules 14, and the plurality of cropping modules 15 may be realized via wired or wireless connections.

In use, the image processing device 100 is configured to implement a method for categorizing and adjusting an orientation of a clinical image. In this embodiment, the clinical images may be facial images and/or intra-oral images of a patient.

Figure 2:
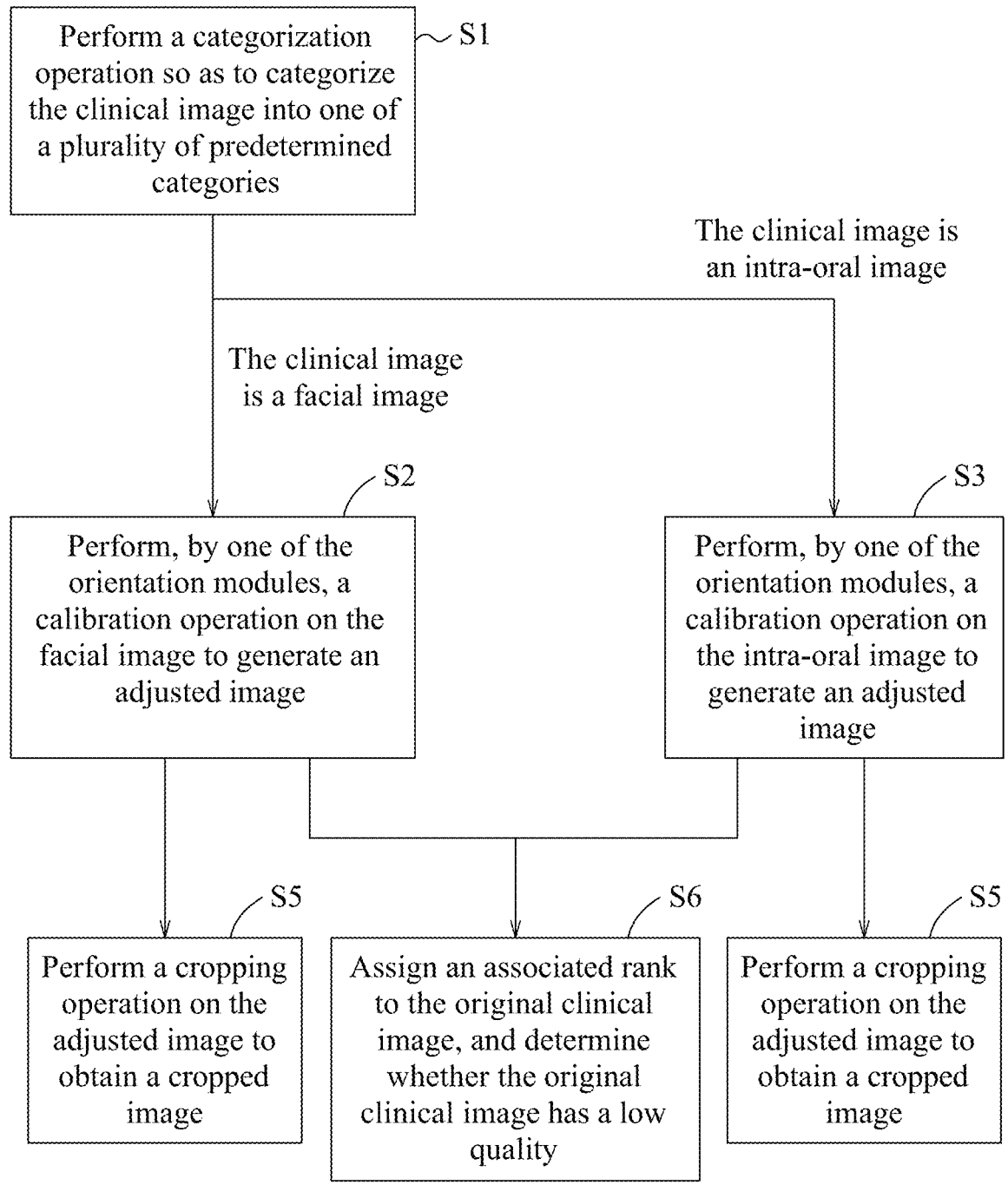
FIG. 2 is a flow chart illustrating steps of a method for categorizing and adjusting an orientation of a clinical image according to one embodiment of the disclosure.

FIG. 2 is a flow chart illustrating steps of a method for categorizing and adjusting an orientation of a clinical image according to one embodiment of the disclosure. In this embodiment, the method is implemented using the image processing device 100 of FIG. 1.

Figure 3:
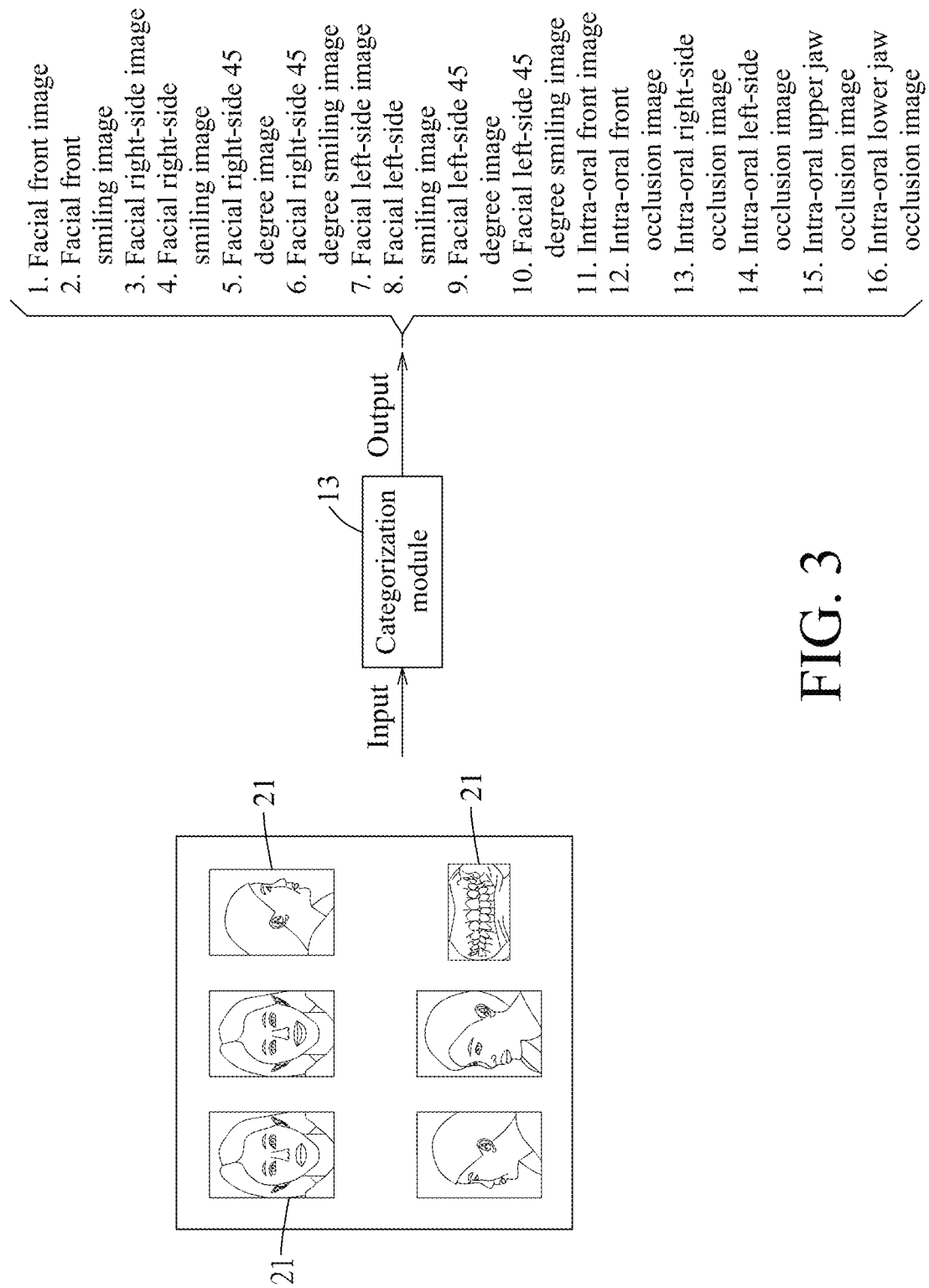
FIG. 3 illustrates operations of a categorization module that receives clinical images as input.

Firstly, the processor 11 receives a plurality of clinical images 21 (see FIG. 3). It is noted that in embodiments, the clinical images 21 may be pre-stored in the data storage module 12, or may be obtained from an external source (e.g., a network such as the Internet) via the communication unit 17. In some embodiments, the clinical images 21 are digital images captured by digital cameras. It is noted that other images associated with the fields of, for example plastic surgical department, dermatological department, etc., that contain a human face or the inside of the oral cavity may also serve as the clinical images 21.

Further referring to FIG. 3, in step S1, the categorization module 13 performs a categorization operation so as to categorize each of the clinical images 21 into one of a plurality of predetermined categories.

Specifically, in this embodiment, the categorization module 13 includes a pre-trained neural network model such as a convolutional neural network (CNN) model. The CNN model may be trained using a large number of clinical images each with a designated category and a number of features that can be identified. In this embodiment, sixteen predetermined categories are present, where ten of the sixteen predetermined categories are related to facial images (i.e., images of the face of the patient taken from outside of the oral cavity of the patient to show facial features of the patient) and six of the sixteen predetermined categories are related to intra-oral images (i.e., images taken to show the inside of the oral cavity of the patient). As such, sixteen orientation modules 14, and sixteen cropping modules 15 are present in the embodiment of FIG. 1.

In the example of FIG. 3, sixteen clinical images 21 are present, each of the clinical images 21 is applied to the pre-trained neural network model of the categorization module 13 as an input, and the categorization module 13 outputs one of the sixteen predetermined categories for each of the clinical images 21. As such, each of the clinical images 21 may be categorized into one of the sixteen predetermined categories outputted by the categorization module 13 for subsequent processing.

After the clinical images 21 are categorized, each of the clinical images 21 is transmitted to a corresponding one of the plurality of orientation modules 14 based on the result of the categorization operation (i.e., based on the corresponding predetermined category the clinical image 21 is categorized into). Each of the plurality of orientation modules 14, in response to receipt of one of the clinical images 21, is configured to perform an orientation adjusting operation (i.e., image straightening).

It is noted that in some embodiments, when it is determined that one of the clinical images 21 cannot be categorized into any one of the predetermined categories, the categorization module 13 may output an "unknown" result indicating that the one of the clinical images 21 cannot be categorized. As such, the one of the clinical images 21 may be labeled with an unknown category and stored in a specific directory in the data storage module 12 for subsequent processing using other means such as manual categorization.

It is noted that in this embodiment, the sixteen predetermined categories may be classified into two distinct groups: a group relating to facial images and a group relating to intra-oral images. For each of the two groups, a specific manner of orientation operation is to be performed. As such, in the embodiment of FIG. 1, ten first orientation modules 14A and six second orientation modules 14B are present for handling the facial images and the intra-oral images, respectively. Similarly, ten first cropping modules 15A and six second cropping modules 15B are present for handling the facial images and the intra-oral images, respectively. Each of the ten first orientation modules 14A is connected to a respective one of the ten first cropping modules 15A, and each of the six second orientation modules 14B is connected to a respective one of the six second cropping modules 15B.

Figure 4:
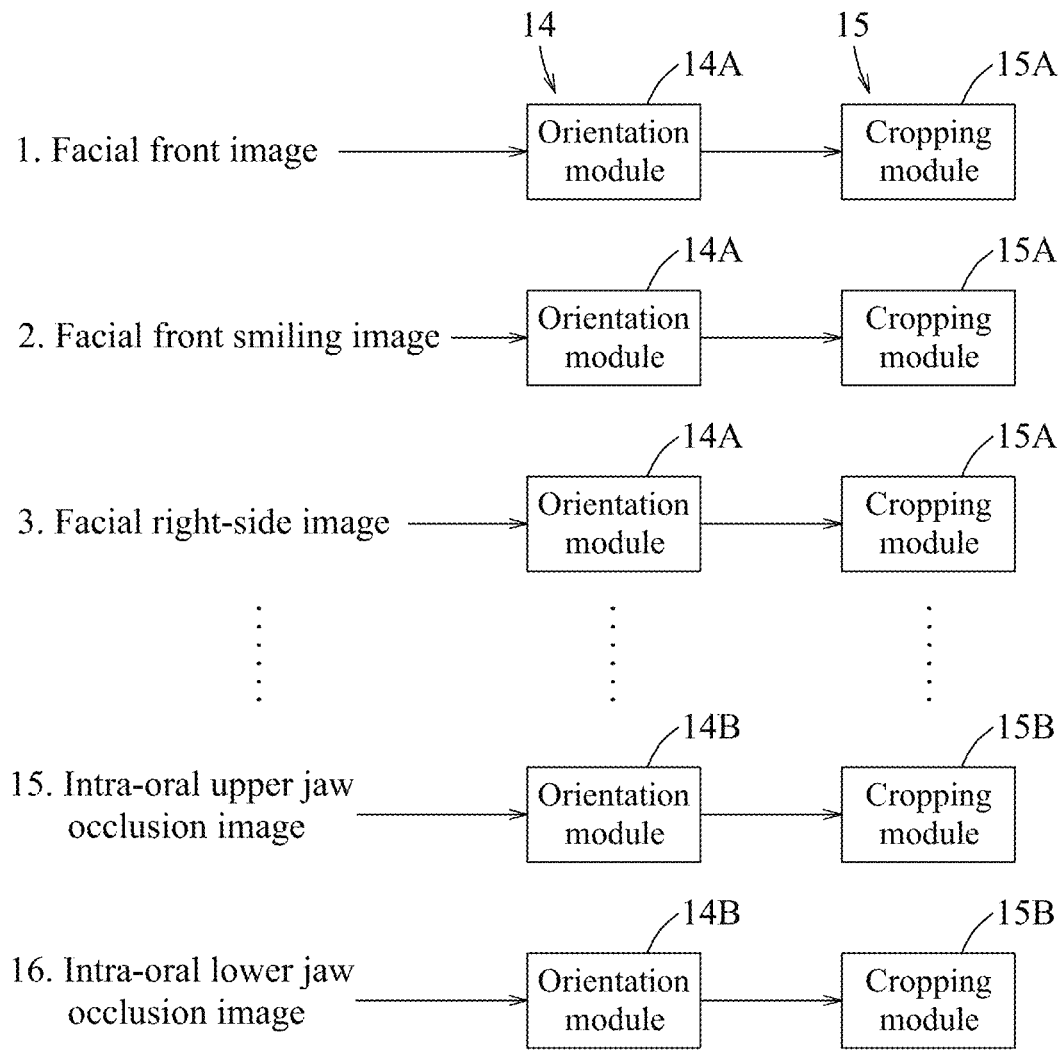
FIG. 4 illustrates a number of exemplary predetermined categories of the clinical images, and the associated components for processing the clinical images.

FIG. 4 illustrates a number of exemplary predetermined categories, and, for each category, the associated components for processing any clinical image 21 categorized into that category. As shown in FIG. 4, the predetermined categories "facial front image," "facial front smiling image," "facial right-side image," etc., relate to facial images, and a clinical image 21 that is categorized into one of these predetermined categories will be transmitted to a corresponding one of the first orientation modules 14A (and subsequently to a connected first cropping module 15A). On the other hand, the predetermined categories "intra-oral upper jaw occlusion image," "intra-oral lower jaw occlusion image," etc., relate to intra-oral images, and a clinical image 21 that is categorized into one of these predetermined categories will be transmitted to a corresponding one of the second orientation modules 14B (and subsequently to a connected second cropping module 15B). In the case of a facial image, the orientation adjusting operation is performed by one of the first orientation modules 14A in step S2.

Figure 5:
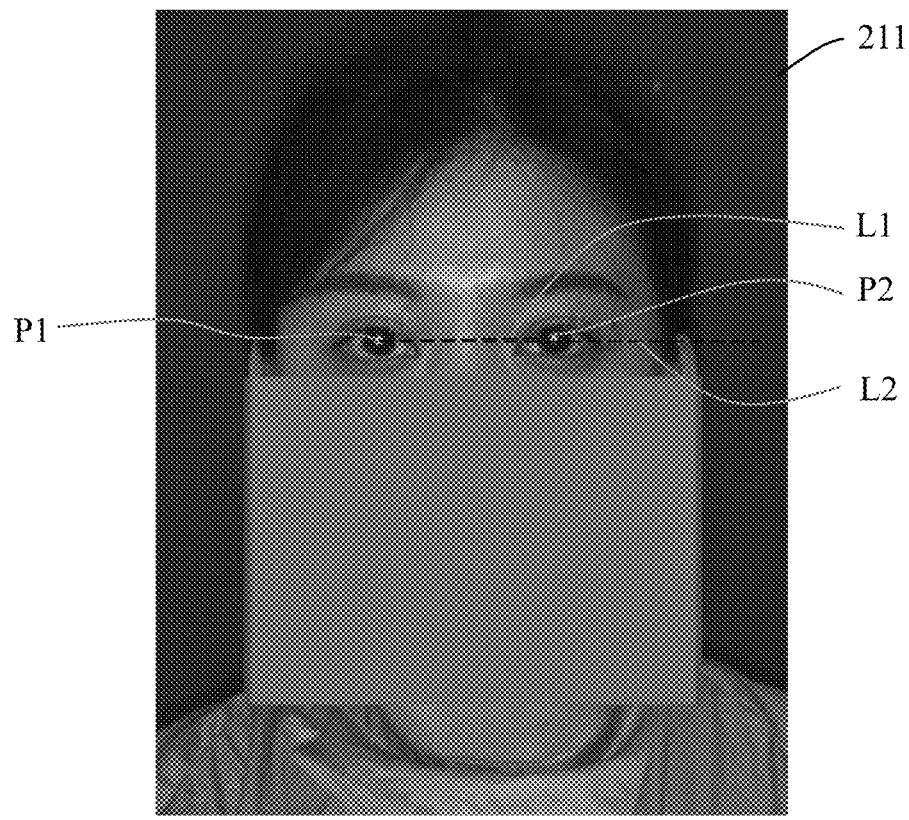
FIG. 5 illustrates an exemplary clinical image, which may be categorized by the categorization module as a facial front image of a human face.

FIG. 5 illustrates an exemplary clinical image 211, which may be categorized by the categorization module 13 as a facial front image of a human face, which belongs to a facial image. As such, the categorization module 13 may transmit the clinical image 211 to a corresponding one of the first orientation modules 14A that corresponds to a "facial front image" category. Note that in this and other exemplary clinical images, some facial features of the person shown in the exemplary clinical images are blocked to conceal and protect the identity of this person.

Then, in step S2, the corresponding one of the first orientation modules 14A identifies an object in the clinical image 211 (e.g., a human face), and identifies two feature points P1, P2 on the object. In the example of FIG. 5, the two feature points P1, P2 are white or bright spots in the two pupils of the human face. Afterward, the corresponding one of the first orientation modules 14A generates a feature line L1 that connects the two feature points P1, P2 and generates a reference line L2 that passes through one of the two feature points (e.g., P1) and that extends in parallel with an X axis associated with a reference coordinate system of the clinical image 211.

Then, the corresponding one of the first orientation modules 14A determines whether the feature line L1 and the reference line L2 overlap each other (that is, whether the feature line L1 extends in parallel with the X axis). In the case where it is determined that the feature line L1 and the reference line L2 overlap each other, it may be determined that no orientation calibration is needed, as the clinical image 211 is already properly oriented, and the orientation adjusting operation is completed. Otherwise, in the case where it is determined that the feature line L1 and the reference line L2 do not overlap each other, the corresponding one of the first orientation modules 14A rotates the clinical image 211, using the one of the two feature points (i.e., P1, through which the reference line L2 passes) as a pivot, such that the feature line L1 overlaps the reference line L2. Specifically, in the example of FIG. 5, a right side of the feature line L1 is more elevated compared to the reference line L2, and as a result, the corresponding one of the first orientation modules 14A would rotate the clinical image 211 clockwise. As the clinical image 211 is rotated clockwise, since the feature point P1 remains stationary, and the feature point P2 is moved downward, the feature line L1 is rotated clockwise, while the reference line L2 remains stationary (since the feature point P1 and the X axis remain stationary). As such, the feature line L1 is rotated toward the reference line L2 to the point where the feature line L1 and the reference line L2 overlap each other (i.e., both the two feature points P1, P2 are located on the reference line L2). At this point, the orientation adjusting operation is completed. A resulting adjusted image is then stored.

Figure 6:
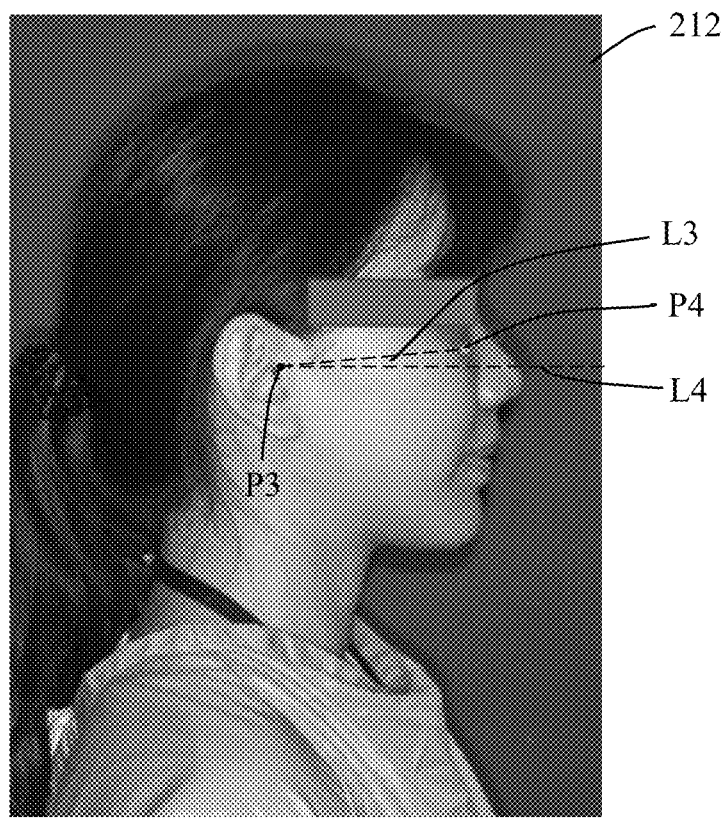
FIG. 6 illustrates an exemplary clinical image, which may be categorized by the categorization module as a facial right-side image of a human face.

FIG. 6 illustrates an exemplary clinical image 212, which may be categorized by the categorization module 13 as a facial right-side image of a human face, which belongs to a facial image. As such, the categorization module 13 may transmit the clinical image 212 to another one of the first orientation modules 14A that corresponds to a "facial right-side image" category.

Then, in step S2, the another one of the first orientation modules 14A identifies an object in the clinical image 212 (e.g., a human face in profile), and identifies two feature points P3, P4 on the object. In the example of FIG. 6, the feature point P3 is a highest point of a tragus on the human face, and the feature point P4 is a specific point of an under-eye-swelling (also known as lower eyelid "love band") of the human face (e.g., a lowest point of the under-eye-swelling). Afterward, the another one of the first orientation modules 14A generates a feature line L3 that connects the two feature points P3, P4 and generates a reference line L4 that passes through one of the two feature points (e.g., P3) and that extends in parallel with an X axis associated with a reference coordinate system of the clinical image 212.

Then, the another one of the first orientation modules 14A determines whether the feature line L3 and the reference line L4 overlap each other (that is, whether the feature line L3 extends in parallel with the X axis). In the case where it is determined that the feature line L3 and the reference line L4 overlap each other, it may be determined that no orientation calibration is needed, as the clinical image 212 is already properly oriented, and the orientation adjusting operation is completed. Otherwise, in the case where it is determined that the feature line L3 and the reference line L4 do not overlap each other, the another one of the first orientation modules 14A rotates the clinical image 212, using the one of the two feature points (i.e., P3) as a pivot, such that the feature line L3 overlaps the reference line L4. Specifically, in the example of FIG. 6, the right side of the feature line L3 is more elevated compared to the reference line L4, and as a result, the another one of the first orientation modules 14A would rotate the clinical image 212 clockwise. During the clockwise rotation of the clinical image 212, since the feature point P3 remains stationary, and the feature point P4 is moved downward, the feature line L3 is also rotated clockwise, while the reference line L4 remains stationary. As such, the feature line L3 is rotated toward the reference line L4 to the point where the feature line L3 and the reference line L4 overlap each other (i.e., both the two feature points P3, P4 are located on the reference line L4). At this point, the orientation adjusting operation is completed. A resulting adjusted image is then stored.

In this embodiment, each of the first orientation modules 14A includes a pre-trained neural network model. The neural network model may be one that uses a deep neural network model as a backbone and that is configured to perform classification operations, such as a CNN model or a CNN regression model, or one that employs deep learning for performing segmentation and keypoint detection, such as a fully convolutional network, a semantic segmentation model (SegNet), DeepLab, RefineNet, PSPNet, Unet, Unet++, etc. The neural network model is trained using facial images with pre-labeled feature points, and is then configured to identify feature points on the clinical images received from the categorization module 13. As such, each of the first orientation modules 14A is configured to perform the operations of step S2.

On the other hand, in the case of an intra-oral image, the orientation adjusting operation is performed by one of the second orientation modules 14B in step S3.

Figure 7:
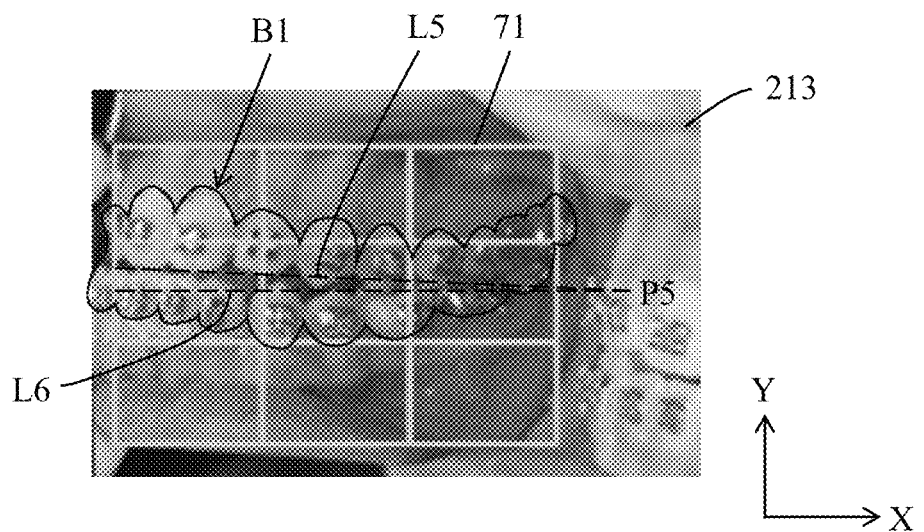
FIG. 7 illustrates an exemplary clinical image, which may be categorized by the categorization module as an intra-oral right side occlusion image.

FIG. 7 illustrates an exemplary clinical image 213, which may be categorized by the categorization module 13 as an intra-oral right side occlusion image, which belongs to an intra-oral image. As such, the categorization module 13 may transmit the clinical image 213 to a corresponding one of the second orientation modules 14B that corresponds to an "intra-oral right side occlusion image" category. It is noted that the clinical image 213 is a dental photograph taken using a mirror, but the system of the embodiment is capable of processing both images that are taken directly and images that are taken using a mirror.

Then, in step S3, the corresponding one of the second orientation modules 14B identifies an object (e.g., dental arches in the oral cavity) in the clinical image 213, and identifies a feature area B1 in the clinical image 213 that encloses the object, based on a contour of the object. Afterward, the corresponding one of the second orientation module 14B generates a feature line L5 that divides the object into an upper part and a lower part, superimposes a reference frame 71 on the object, and generates a reference line L6 that evenly divides the reference frame 71 into two halves (e.g., an upper half and a lower half). In examples, the feature line L5 is generated such that the upper part and the lower part of the object are substantially symmetrical with each other about the feature line L5, the reference frame 71 is in the form of a nine-box grid and includes horizontal lines extending in parallel with an X axis associated with a reference coordinate system of the clinical image 213 and vertical lines extending in parallel with a Y axis associated with the reference coordinate system, and the reference line L6 is a horizontal line that extends in parallel with the X axis.

Then, the corresponding one of the second orientation modules 14B determines whether the feature line L5 and the reference line L6 overlap each other. In the case where it is determined that the feature line L5 and the reference line L6 overlap each other, it may be determined that no orientation calibration is needed, as the clinical image 213 is already properly oriented, and the orientation adjusting operation is completed. Otherwise, in the case where it is determined that the feature line L5 and the reference line L6 do not overlap each other, the corresponding one of the second orientation modules 14B would rotate the clinical image 213, using an intersection point of the feature line L5 and the reference line L6 (labeled P5) as a pivot, such that the feature line L5 overlaps the reference line L6. Specifically, in the example of FIG. 7, a left side of the feature line L5 is more elevated compared to the reference line L6, and as a result, the corresponding one of the second orientation modules 14B would rotate the clinical image 213 counterclockwise. As the clinical image 213 is rotated counterclockwise, since the reference line L6 remains stationary, and the feature line L5 is rotated counterclockwise, the feature line L5 is rotated toward the reference line L6 to the point where the feature line L5 and the reference line L6 overlap each other (i.e., both the feature line L5 and the reference line L6 are parallel to the X axis). At this point, the orientation adjusting operation is completed. A resulting adjusted image is then stored.

Figure 8:
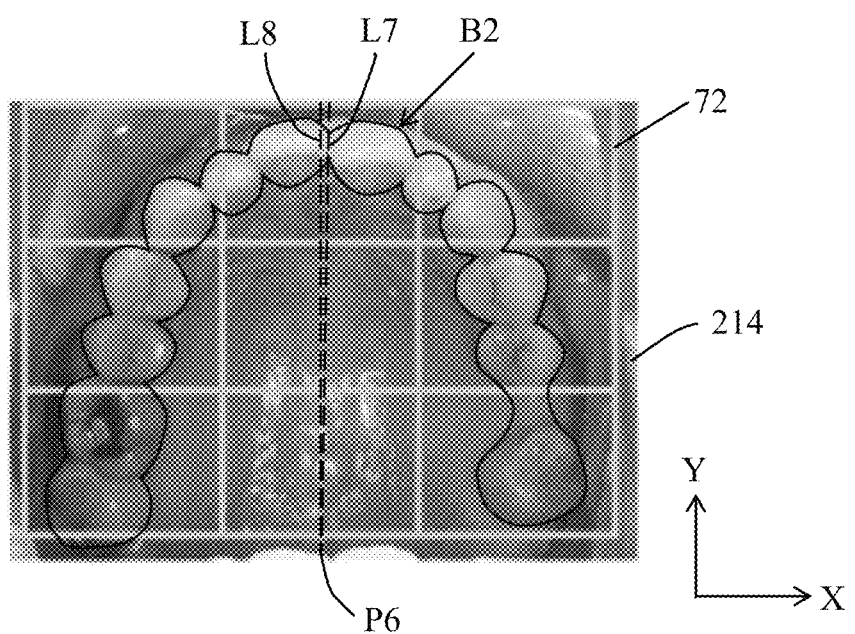
FIG. 8 illustrates an exemplary clinical image, which may be categorized by the categorization module as an intra-oral upper jaw occlusion image.

FIG. 8 illustrates an exemplary clinical image 214, which may be categorized by the categorization module 13 as an intra-oral upper jaw occlusion image, which belongs to an intra-oral image. As such, the categorization module 13 may transmit the clinical image 214 to another one of the second orientation modules 14B that corresponds to an "intra-oral upper jaw occlusion image" category.

Then, in step S3, the another one of the second orientation modules 14B identifies an object (i.e., a dental arch in the oral cavity) in the clinical image 214, and identifies a feature area B2 in the clinical image 214 that encloses the object, based on a contour of the object. Afterward, the another one of the second orientation module 14B generates a feature line L7 that divides the object into a left part and a right part, superimposes a reference frame 72 on the object, and generates a reference line L8 that evenly divides the reference frame 72 into a left half and a right half. In examples, the feature line L7 is generated such that the left part and the right part of the object are substantially symmetrical with each other about the feature line L7, the reference frame 72 is in the form of a nine-box grid and includes horizontal lines extending in parallel with an X axis associated with a reference coordinate system of the clinical image 214 and vertical lines extending in parallel with a Y axis associated with the reference coordinate system, and the reference line L8 is a vertical line that extends in parallel with the Y axis.

Then, the another one of the second orientation modules 14B determines whether the feature line L7 and the reference line L8 overlap each other. In the case where it is determined that the feature line L7 and the reference line L8 overlap each other, it may be determined that no orientation calibration is needed, as the clinical image 214 is already properly oriented, and the orientation adjusting operation is completed. Otherwise, in the case where it is determined that the feature line L7 and the reference line L8 do not overlap each other, the another one of the second orientation modules 14B would rotate the clinical image 214, using an intersection point of the feature line L7 and the reference line L8 (labeled P6) as a pivot, such that the feature line L7 overlaps the reference line L8. Specifically, in the example of FIG. 8, the feature line L7 is inclined rightward compared to the reference line L8, and as a result, the another one of the second orientation modules 14B would rotate the clinical image 214 counterclockwise. During counterclockwise rotation of the clinical image 214, since the reference line L8 remains stationary, and the feature line L7 is rotated counterclockwise, the feature line L7 is rotated toward the reference line L8 to the point where the feature line L7 and the reference line L8 overlap each other (i.e., both the feature line L7 and the reference line L8 are parallel to the Y axis). At this point, the orientation adjusting operation is completed. A resulting adjusted image is then stored.

In this embodiment, each of the second orientation modules 14B includes a pre-trained neural network model. The neural network model may be one that uses a deep neural network model as a backbone and that is configured to perform classification operations, such as a CNN model or a CNN regression model, or one that employs deep learning for performing segmentation and keypoint detection, such as a fully convolutional network, a semantic segmentation model (SegNet), DeepLab, RefineNet, PSPNet, Unet, Unet++, etc. The neural network model is trained using intra-oral images each with a pre-labeled feature area, and is then configured to identify a feature area on the clinical image received from the categorization module 13. As such, each of the second orientation modules 14B is configured to perform the operations of step S3.

After the orientation adjusting operation is completed, the resulting adjusted image is transmitted to a connected one of the cropping modules 15 for performing a cropping operation. Similar to the orientation adjusting operation, depending on which of a facial image and an intra-oral image the adjusted image is originally, different manners of the cropping operation will be implemented.

Figure 9:
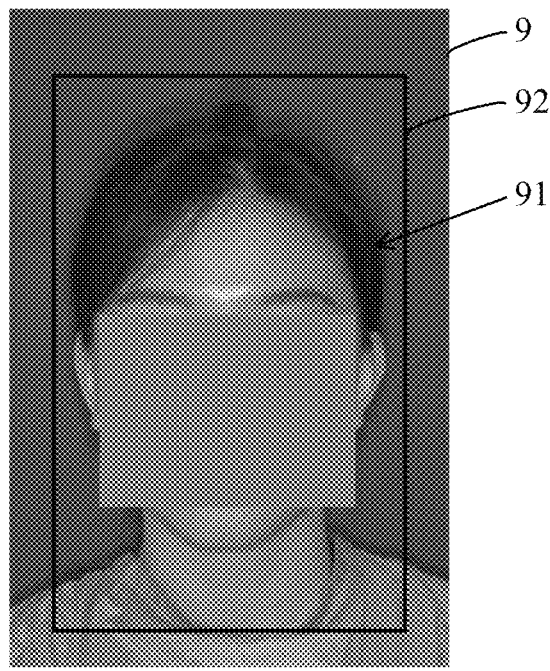
FIG. 9 illustrates an adjusted image which is generated based on the clinical image of FIG. 5.

For example, FIG. 9 illustrates an adjusted image 9, which is generated based on the clinical image 211 (belonging to a facial image). In response to receipt of the adjusted image 9, in step S4, one of the first cropping modules 15A that is connected to the corresponding one of the first orientation modules 14A which processed the clinical image 211 (see FIG. 4) identifies an object 91 (e.g., the human face) in the adjusted image 9, and determines a crop frame 92 based on the object 91. In this embodiment, the crop frame 92 is determined by defining a minimal bounding rectangle that encloses the object, and "expanding" the minimal bounding rectangle with respect to each of an upper edge, a lower edge, a left edge and a right edge of the minimal bounding rectangle to obtain another rectangle that serves as the crop frame 92. In this embodiment, the crop frame 92 is obtained by expanding the minimal bounding rectangle by about 5 to 10 pixels with respect to each of the upper edge, the lower edge, the left edge and the right edge of the minimal bounding rectangle. However, in other embodiments, the crop frame 92 may be obtained by expanding the minimal bounding rectangle by other number of pixels with respect to each of the upper edge, the lower edge, the left edge and the right edge of the minimal bounding rectangle, according to user preferences.

Figure 10:
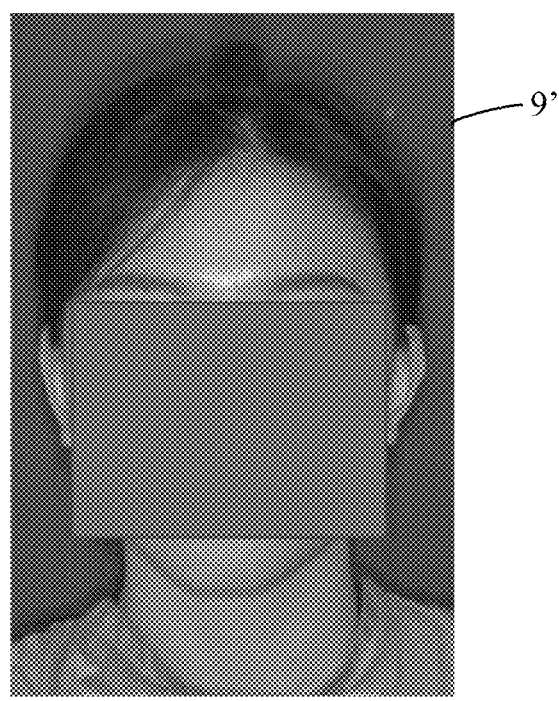
FIG. 10 illustrates an exemplary cropped image generated from the adjusted image of FIG. 9.

Then, the one of the first cropping modules 15A obtains a cropped image from the adjusted image 9 by cutting off parts of the adjusted image 9 that are outside the crop frame 92, and storing the remaining part of the adjusted image 9 as the cropped image. FIG. 10 illustrates an exemplary cropped image 9'.

In this embodiment, each of the first cropping modules 15A includes a pre-trained neural network model. The neural network model may be one that uses deep neural network model as a backbone and that is configured to perform object detection operations, such as a Fast R-CNN model, a single shot multibox detector (SSD), a mask R-CNN model, you only look once (YOLO) v1-v4 models, etc. The neural network model is trained using facial images that have been cropped, and is then configured to identify the object, define the minimal boundary rectangle, and obtain the crop frame 92 for the adjusted images received from the connected first orientation module 14A. As such, each of the first cropping modules 15A is configured to perform the operations of step S4.

Figure 11:
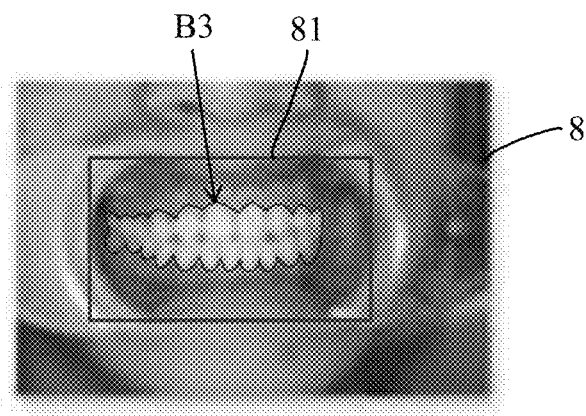
FIG. 11 illustrates an adjusted image which is generated based on another clinical image.

For example, FIG. 11 illustrates an adjusted image 8, which is generated based on a clinical image that is an intra-oral front occlusion image (belonging to an intra-oral image). In response to receipt of the adjusted image 8, in step S5, one of the second cropping modules 15B that is connected to one of the second orientation modules 14B which processed the clinical image to obtain the adjusted image 8 is configured to identify an object B3 (e.g., dental arches in the oral cavity) in the adjusted image 8, and to determine a crop frame 81 based on the object B3. In this embodiment, the crop frame 81 is determined by defining a rectangle that encloses the object B3 and that serves as the crop frame 81. In this embodiment, the crop frame 81 is obtained by defining a minimal bounding rectangle that has four edges spaced apart from the object B3 by preset distances such that an upper lip and a lower lip can be included in the minimal bounding rectangle.

Figure 12:
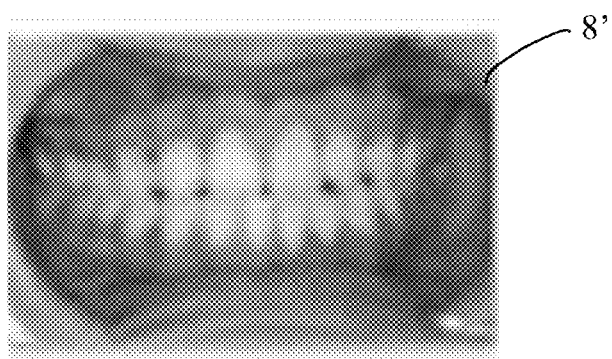
FIG. 12 illustrates an exemplary cropped image generated from the adjusted image of FIG. 11.

Then, the one of the second cropping modules 15B is configured to obtain a cropped image from the adjusted image 8 by cutting off parts of the adjusted image 8 outside the crop frame 81, and storing a remaining part of the adjusted image 8 as the cropped image. FIG. 12 illustrates an exemplary cropped image 8'.

In this embodiment, each of the second cropping modules 15B includes a pre-trained neural network model. The neural network model may be one that uses deep neural network model as a backbone and that is configured to perform object detection operations, such as a Fast R-CNN model, a single shot multibox detector (SSD), a mask R-CNN model, you only look once (YOLO) v1-v4 models, etc. The neural network model is trained using intra-oral images that have been cropped, and is then configured to identify the object, define the minimal boundary rectangle, and obtain the crop frame 81 on the adjusted images received from the connected second orientation module 14B. As such, each of the second cropping modules 15B is configured to perform the operations of step S5.

After the cropping operations are completed, a number of cropped images may be obtained and then stored. As such, for each of the predetermined categories, the clinical images may be properly oriented and cropped to have a similar size.

It is noted that in some embodiments, the image processing device 100 may further include a ranking module 16 (see FIG. 1). The ranking module 16 may be embodied using software instructions that can be integrated into a software application stored in the data storage module 12. When executed by the processor 11, the software application causes the processor 11 to perform operations as described in the following paragraphs.

In use, the ranking module 16 is connected to each of the plurality of orientation modules 14. After an adjusted image is generated by one of the orientation modules 14 in steps S3 or S4, the ranking module 16 may determine, in step S6, a rotation angle of the adjusted image relative to the original clinical image, and assign an associated rank to the original clinical image based on the rotation angle thus determined. For example, when it is determined that the adjusted image is rotated by more than a predetermined angle (e.g., 10 degrees) relative to the original clinical image, it may be deduced that the original clinical image is tilted and therefore needs substantial processing. As such, the original clinical image may be assigned a lower rank, but the operations of the ranking module 16 are not limited as such. In some embodiments, the ranking module 16 is configured to determine whether an image has a low quality. The determination may include determining whether the feature points cannot be identified (in the case for the facial image), the feature area cannot be identified (in the case for the intra-oral image), or whether the feature area is interrupted or blocked by a foreign object (in the case for the intra-oral image), etc. In any one of the above cases, the ranking module 16 assigns a lower rank to the image, indicating that the image has a low quality.

It is noted that in some embodiments, the cropping modules 15 or the ranking module 16 may be omitted. As such, the operations of steps S4 and S5 may be omitted from the method illustrated in FIG. 2.

According to one embodiment of the disclosure, there is provided a non-transitory machine readable storage medium. The non-transitory machine readable storage medium stores instructions that, when executed by a processor of a computer device, cause the processor to perform steps of a method for categorizing and adjusting an orientation of a clinical image as illustrated in FIG. 2.

To sum up, the embodiments of the disclosure provide a method, a system and a non-transitory machine readable storage medium for categorizing and adjusting an orientation of a clinical image. In the method, in response to receipt of a clinical image, a categorization module is configured to determine one of several predetermined categories for the clinical image. Then, the clinical image is transmitted to a corresponding one of a plurality of orientation modules, which is configured to determine whether the clinical image is properly oriented (by comparing a feature line and a reference line generated based on the clinical image). When it is determined that the clinical image is not properly oriented, the corresponding one of the orientation modules is configured to rotate the clinical image based on the feature line and the reference line, so as to generate an adjusted image that is properly oriented. In this manner, a large number of clinical images may be automatically categorized and adjusted to have proper orientations (i.e., straightened) for subsequent processing or utilization. In some embodiments, with respect to each of the predetermined categories, the adjusted images may be further cropped to have a substantially uniform size.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for categorizing and adjusting an orientation of a clinical image, the method being implemented using a system that includes a categorization module, a plurality of orientation modules, and a plurality of cropping modules that are connected to the plurality of orientation modules, respectively, the method comprising:
   a) in response to receipt of the clinical image, performing, by the categorization module, a categorization operation so as to categorize the clinical image into one of a plurality of predetermined categories;
   b) transmitting the clinical image to a corresponding one of the plurality of orientation modules based on a result of the categorization operation; and
   c) performing, by the corresponding one of the plurality of orientation modules, an orientation adjusting operation for adjusting the orientation of the clinical image,
   wherein the orientation adjusting operation includes
      c-1) in the case where it is determined, based on the categorization operation, that the clinical image is a facial image,
         identifying an object in the clinical image,
         identifying two feature points on the object,
         generating a feature line that connects the two feature points, and a reference line that passes through one of the two feature points, that extends in parallel with an axis associated with a reference coordinate system of the clinical image,
         determining whether the feature line and the reference line overlap each other, and
         in the case where the feature line and the reference line are determined as not overlapping each other, rotating the clinical image, using the one of the two feature points through which the reference line passes as a pivot, to the point where the feature line overlaps the reference line, so as to generate an adjusted image,
      c-2) in the case where it is determined, based on the categorization operation, that the clinical image is an intra-oral image,
         identifying an object in the clinical image,
         identifying a feature area of the clinical image that encloses the object, based on a contour of the object,
         generating a feature line that divides the object into an upper part and a lower part, and generating a reference line that extends in parallel with one of an X axis and a Y axis associated with the reference coordinate system of the clinical image,
         determining whether the feature line and the reference line overlap each other,
         in the case where it is determined that the feature line and the reference line do not overlap each other, rotating the clinical image using an intersection point of the feature line and the reference line as a pivot, to the point where the feature line and the reference line overlap each other, so as to generate an adjusted image;
   the method further comprising a step of, after step c): d) performing, by one of the cropping modules that is connected to the corresponding one of the orientation modules, a cropping operation that includes
      identifying an object in the adjusted image,
      determining a crop frame that encloses the object, and
      obtaining a cropped image from the adjusted image by cutting off parts of the adjusted image outside the crop frame, and storing a remaining part of the adjusted image as a cropped image;
   wherein:
      step a) includes using a pre-trained neural network model to perform the categorization operation;
      sub-step c-1) includes using a pre-trained neural network model to perform the orientation adjusting operation; and
      step d) includes using a pre-trained neural network model to perform the cropping operation.

2. The method as claimed in claim 1, wherein in sub-step c-2), the reference line is generated by:
  superimposing a reference frame on the object, the reference frame being in the form of a nine-box grid and including horizontal lines that extend in parallel with the X axis and vertical lines that extend in parallel with the Y axis; and
  generating the reference line that evenly divides the reference frame into two halves.

3. The method as claimed in claim 1, wherein:
  sub-step c-2) includes using a pre-trained neural network model to perform the orientation adjusting operation.

4. The method as claimed in claim 1, further comprising:
  determining a rotation angle of the adjusted image with respect to the clinical image, and assigning an associated rank to the clinical image based on the adjusted image; and
  determining whether an image has a low quality, and in the case that the determination is affirmative, assigning a low rank to the image indicating that the image has a low quality,
  wherein the determining of whether an image has a low quality includes determining whether the feature points or the feature area can be identified, or whether the feature area is interrupted by a foreign object.

5. A system for categorizing and adjusting an orientation of a clinical image, the system comprising a categorization module, a plurality of orientation modules connected to the categorization module, a data storage module that stores the clinical therein, and a plurality of cropping modules that are connected with the plurality of orientation modules, respectively, wherein:
  in response to receipt of the clinical image, the categorization module is configured to perform a categorization operation so as to categorize the clinical image into one of a plurality of predetermined categories, and to transmit the clinical image to a corresponding one of the plurality of orientation modules based on a result of the categorization operation;
  the corresponding one of the plurality of orientation modules is configured to perform an orientation adjusting operation for adjusting the orientation of the clinical image, the orientation adjusting operation including
    in the case that it is determined that, based on the categorization operation, the clinical image is a facial image,
      identifying an object in the clinical image,
      identifying two feature points on the object,
      generating a feature line that connects the two feature points and a reference line that passes through one of the two feature points, that extends in parallel with an axis associated with a reference coordinate system of the clinical image,
      determining whether the feature line and the reference line overlap each other, and
      in the case that the feature line and the reference line are determined as not overlapping each other, rotating the clinical image, using the one of the two feature points through which the reference line passes as a central point of rotation, to the point that the feature line overlaps the reference line, so as to generate an adjusted image,
    in the case that it is determined that, based on the categorization operation, the clinical image is an intra-oral image,
      identifying an object in the clinical image,
      identifying a feature area of the clinical image that encloses the object, based on a contour of the object,
      generating a feature line that divides the object into an upper part and a lower part, and generating a reference line that extends in parallel with one of an X axis and a Y axis associated with the reference coordinate system of the clinical image,
      determining whether the feature line and the reference line overlap each other,
      in the case that it is determined that the feature line and the reference line do not overlap each other, rotating the clinical image using an intersection point of the feature line and the reference line as a central point of rotation, to the point that the feature line and the reference line overlap each other, so as to generate an adjusted image;
  wherein each of the plurality of cropping modules is configured to, after the orientation adjusting operation, perform a cropping operation that includes
    identifying an object in the adjusted image,
    determining a crop frame that encloses the object, and
    obtaining a cropped image from the adjusted image by cutting off parts of the adjusted image outside the crop frame, and storing a remaining part of the adjusted image as a cropped image;
  wherein:
    the categorization module includes a pre-trained neural network model for performing the categorization operation;
    in the case that it is determined that the clinical image is a facial image, the corresponding one of the plurality of orientation modules includes a pre-trained neural network model for performing the orientation adjusting operation; and
    each of the plurality of cropping modules includes a pre-trained neural network model for performing the orientation adjusting operation.

6. The system as claimed in claim 5, wherein the corresponding one of the plurality of orientation modules is configured to generate the reference line by:
  applying a reference frame onto the object, the reference frame being in the form of a nine-square division and including horizontal lines extending in parallel with the X axis and vertical lines extending in parallel with the Y axis; and
  generating the reference line that evenly divides the reference frame into two halves.

7. The system as claimed in claim 5, wherein: in the case that it is determined that the clinical image is an intra-oral image, the corresponding one of the plurality of orientation modules includes a pre-trained neural network model for performing the orientation adjusting operation.

8. The system as claimed in claim 5, further comprising a ranking module that is configured to:
  determine a rotation angle of the adjusted image with respect to the clinical image, and assign an associated rank to the clinical image based on the adjusted image; and
  determine whether an image has a low quality, and in the case that the determination is affirmative, assign a low rank to the image indicating that the image has a low quality,
  wherein the determining of whether an image has a low quality includes determining whether the feature points or the feature area can be identified, or whether the feature area is interrupted by a foreign object.

9. A non-transitory machine readable storage medium storing instructions that, when executed by a processor of a computer device, cause the processor to perform steps of a method as claimed in claim 1.

\* \* \* \* \*